United States Patent
Coupard et al.

(10) Patent No.: US 9,663,414 B2
(45) Date of Patent: May 30, 2017

(54) PROCESS FOR DEHYDRATION OF ETHANOL TO ETHYLENE AT LOW ENERGY CONSUMPTION

(71) Applicants: IFP ENERGIES NOUVELLES, Rueil-Malmaison (FR); TOTAL RESEARCH & TECHNOLOGY FELUY, Seneffe (BE)

(72) Inventors: Vincent Coupard, Villeurbanne (FR); Natacha Touchais, Vienne (FR); Thomas Plennevaux, Lyons (FR); Emilie Kobel, Chasse sur Rhone (FR); Stephanie Fleurier, Lyons (FR); Walter Vermeiren, Houthalen-Helchteren (BE); Delphine Minoux, Nivelles (BE); Philip De Smedt, Sint-Niklaas (BE); Cindy Adam, Wierde (BE); Nikolai Nesterenko, Nivelles (BE)

(73) Assignees: TOTAL RESEARCH & TECHNOLOGY FELUY, Seneffe (BE); IFP ENERGIES NOUVELLES, Rueil-Malmaison (FR)

(*) Notice: Subject to any disclaimer, the term of this patent is extended or adjusted under 35 U.S.C. 154(b) by 30 days.

(21) Appl. No.: 14/646,877

(22) PCT Filed: Nov. 18, 2013

(86) PCT No.: PCT/FR2013/052767
§ 371 (c)(1),
(2) Date: May 22, 2015

(87) PCT Pub. No.: WO2014/083260
PCT Pub. Date: Jun. 5, 2014

(65) Prior Publication Data
US 2015/0299068 A1    Oct. 22, 2015

(30) Foreign Application Priority Data

Nov. 27, 2012    (FR) ...................... 12 03201

(51) Int. Cl.
*C07C 1/24*       (2006.01)
*C07C 29/76*      (2006.01)
*C07C 41/09*      (2006.01)

(52) U.S. Cl.
CPC .............. *C07C 1/24* (2013.01); *C07C 29/76* (2013.01); *C07C 41/09* (2013.01);
(Continued)

(58) Field of Classification Search
CPC   C07C 1/24; C07C 29/76; C07C 41/09; C07C 11/04; C07C 31/08; C07C 43/06;
(Continued)

(56) References Cited

U.S. PATENT DOCUMENTS 4,396,789 A * 8/1983 Barrocas ............ C07C 1/24
                                                      585/639
9,000,236 B2    4/2015 Minoux et al.
(Continued)

FOREIGN PATENT DOCUMENTS

WO      2010060981 A1    6/2010

OTHER PUBLICATIONS

International Search Report and Search Opinion from PCT/FR2013/052767 dated Apr. 28, 2014.

*Primary Examiner* — Sharon Pregler
(74) *Attorney, Agent, or Firm* — Millen White Zelano and Branigan, PC; Csaba Henter; Anthony Zelano

(57) ABSTRACT

A process for dehydration of an ethanol feedstock to ethylene by:
a) preheating ethanol feedstock by heat exchange with effluent from e), (Continued)

b) pretreating the ethanol feedstock to produce pretreated ethanol feedstock,
c) vaporizing a vaporization feedstock containing pretreated ethanol feedstock and at least a portion of the flow of treated water recycled in an exchanger to produce a vaporized feedstock,
d) compressing said vaporized feedstock to produce a compressed feedstock,
e) dehydrating said compressed feedstock in at least one adiabatic reactor,
f) separating the effluent from the last adiabatic reactor of e) into an effluent containing ethylene and an effluent containing water,
g) purifying at least a portion of the effluent containing water from 0 and separating at least one flow of treated water and at least one flow of unconverted ethanol,
h) recycling at least a portion of the flow of treated water from g) upstream of c).

19 Claims, 1 Drawing Sheet

(52) U.S. Cl.
CPC .... *C07C 2527/173* (2013.01); *C07C 2529/40* (2013.01); *C07C 2529/85* (2013.01)

(58) Field of Classification Search
CPC .......... C07C 2527/173; C07C 2529/40; C07C 2529/85
USPC ................................ 585/638, 639, 640, 641
See application file for complete search history.

(56) References Cited

U.S. PATENT DOCUMENTS 9,085,502 B2 * 7/2015 Coupard ................... C07C 1/24
                                                        585/639
2011/0313213 A1   12/2011 Minoux et al.

* cited by examiner

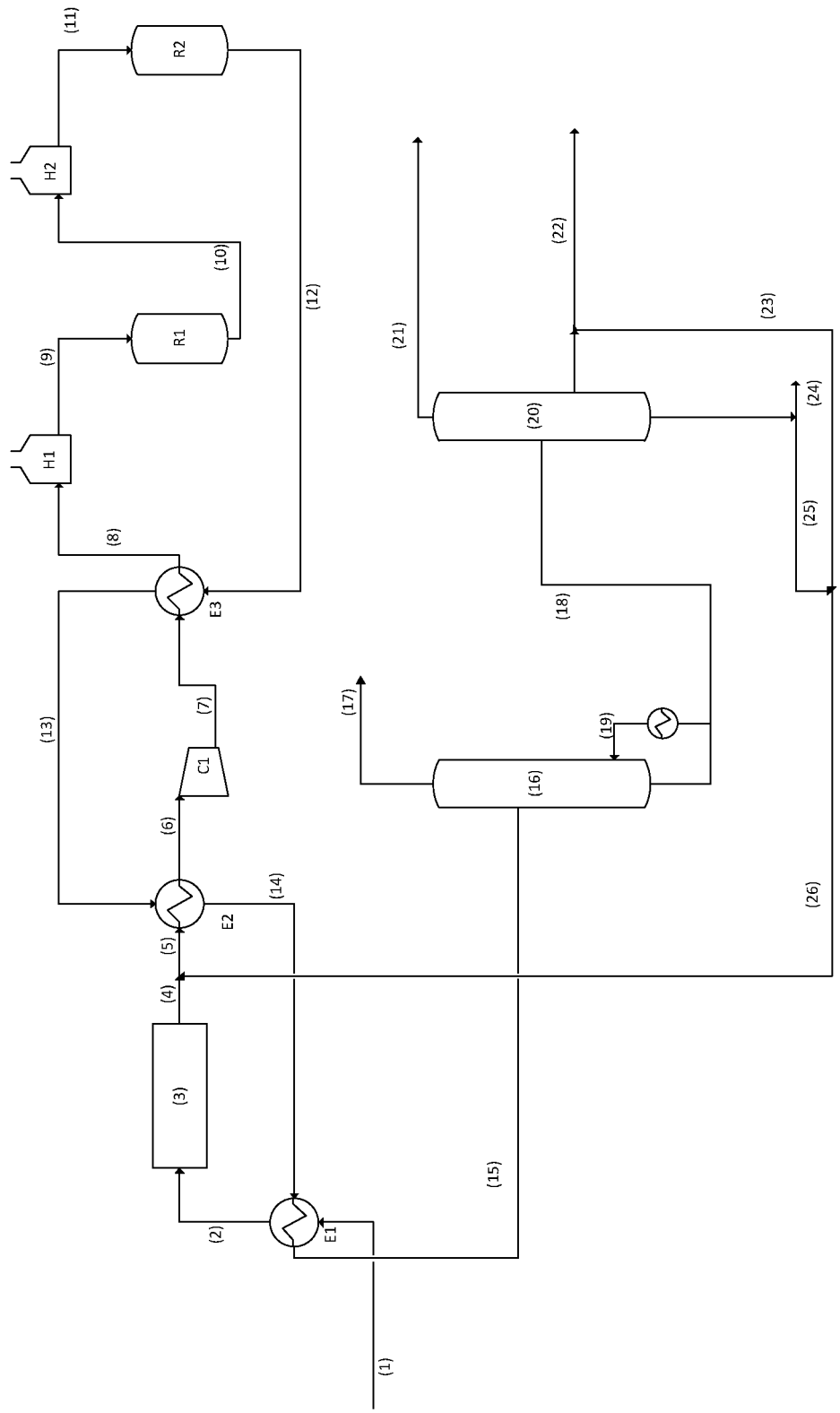

PROCESS FOR DEHYDRATION OF ETHANOL TO ETHYLENE AT LOW ENERGY CONSUMPTION

FIELD OF THE INVENTION

The present invention relates to a process for converting ethanol to ethylene and in particular to a process for dehydration of ethanol.

PRIOR ART

The dehydration reaction of ethanol to ethylene has been known and described in detail since the end of the $19^{th}$ century. "The Dehydration of Alcohols over Alumina. I: The reaction scheme", H. Knözinger, R. Köhne, Journal of Catalysis (1966), 5, 264-270 is regarded as the basic publication for operations of dehydration of alcohols, including ethanol. It is known that this reaction is very endothermic, equilibrated and displaced towards ethylene at high temperature. The temperature drop corresponding to the complete conversion of pure ethanol in an adiabatic reactor is 380° C. At lower temperature, ethanol is converted to diethyl ether (DEE). This reaction "intermediate" may be present in processes for dehydration of ethylene in which the conversion is partial, or between two reactors in multi-reactor processes. DEE can then be converted to ethylene at higher temperature. The reference catalyst often used is a monofunctional acid catalyst, gamma alumina being the catalyst mentioned most. Zeolites are also used for this application, in particular ZSM5 since the 1980s, for example in "Reactions of ethanol over ZSM-5", S. N. Chaudhuri et al., Journal of Molecular Catalysis 62: 289-295 (1990).

U.S. Pat. No. 4,232,179 describes a process for dehydration of ethanol to ethylene in which the heat required for the reaction is supplied by introducing into the reactor a heat-transfer fluid mixed with the feedstock. The heat-transfer fluid is either steam originating from an external source, or an external flow originating from the process, or from recycling a portion of the effluent from the dehydration reactor, i.e. the ethylene produced. Introduction of the mixture of the feedstock with said heat-transfer fluid makes it possible to supply the heat required for maintaining the temperature of the catalyst bed at a level compatible with the desired conversions. In the case where the heat-transfer fluid is the effluent from the dehydration reactor, a compressor for recycling said effluent is necessary. However, the recycling of the ethylene produced by the reaction is a drawback, as the introduction of the ethylene alters the equilibrium of the dehydration reaction. Moreover, ethylene participates in the secondary reactions of oligomerization, of hydrogen transfer and of disproportionation of the olefins, which are reactions of an order greater than 0 with respect to their reagent. The increase in the ethylene concentration from the start of the reaction increases the formation of by-products. The loss of ethylene is therefore greater, which is reflected in a reduction in selectivity.

Patent application WO 2007/134415 describes a process for dehydration of ethanol to ethylene that is improved compared with that of U.S. Pat. No. 4,232,179, making reduced capital expenditure possible, owing to a reduced number of items of equipment and reduced operating costs, because it does not use steam external to the process. In this process, at least a portion of the effluent from the dehydration reactor (mixture of ethylene produced and steam) and superheated steam obtained from the water produced by the dehydration of the ethanol and condensed in the reactor are used as heat-transfer fluid and enter the dehydration reactor mixed with the ethanol. Said patent application says nothing regarding the pressure condition to be respected between the ethanol feedstock and the effluent with the aim of maximizing heat exchange.

U.S. Pat. No. 4,396,789 also describes a process for dehydration of ethanol to ethylene in which ethanol and steam acting as heat-transfer fluid are introduced into the first reactor at a temperature comprised between 400 and 520° C. and at a high pressure comprised between 20 and 40 atm, so that the effluent produced by the dehydration reaction is withdrawn from the last reactor at a pressure at least above 18 atm, said reaction product, i.e. ethylene, being able to undergo, after cooling, the final cryogenic distillation step without an intermediate compression step. Said process is also characterized by heat exchange between said product of the dehydration reaction and the feedstock introduced into the first reactor, said reaction product being used to vaporize the feedstock entering the first reactor. The unconverted ethanol, at least a portion of the water formed during the reactions of the process and the water added for the final scrubbing of the gases are recycled to ensure complete conversion of the ethanol.

Patent application WO 2011/002699 discloses a process for dehydration of an ethanol feedstock to ethylene comprising vaporization of a mixture of ethanol and water and reaction of this mixture in an adiabatic reactor. This application does not address the problem of maximizing heat recovery in order to reduce the energy consumption of the process.

An objective of the invention is to provide a process for dehydration of ethanol to ethylene in which the ethanol feedstock is pretreated using an acidic solid in order to limit the quantity of organic nitrogen, which shortens the catalyst's life, and to convert the ethanol partially to DEE.

An objective of the invention is to provide a process for dehydration of ethanol to high-purity ethylene, said process making it possible to increase the selectivity for ethylene with a specific consumption per tonne of ethylene produced that is lowered significantly compared with the processes of the prior art, as it does not require a heat-transfer fluid external to said process.

SUMMARY AND BENEFIT OF THE INVENTION

The invention describes a process for dehydration of an ethanol feedstock to ethylene comprising in particular a step of pretreatment which reduces the level of organic or basic nitrogen contained in said feedstock and converts a fraction of the ethanol to DEE, and a step of vaporizing the pretreated ethanol feedstock, mixed with at least a portion of a flow of recycled treated water, in an exchanger by means of heat exchange with the effluent from the last dehydration reactor.

Said invention offers the advantage, over the processes of the prior art, of increasing the cycle time of the ethanol dehydration catalyst by trapping the cationic or anionic impurities, the basic, complexing, and chelating impurities, the inorganic or organic impurities, such as for example the nitrogen present in the feedstock in basic form, for example in the form of ammonia and/or organic and basic species, for example in the form of amine, amide, imine or nitrile during the pretreatment step. Trapping the nitrogen-containing compounds has in particular the effect of improving the activity of the acid catalysts used in dehydration.

The present invention also offers the advantage, over the processes of the prior art, of maximizing the heat exchange between the feedstock and the effluent from the last dehydration reactor, i.e. of exchanging all of the enthalpy of vaporization of the feedstock and most of the enthalpy of condensation of said effluent owing to the introduction of the feedstock in the vaporization step c) at a pressure below the pressure of the effluent leaving the last reactor.

The applicant discovered, surprisingly, that said step of pretreatment carried out under the operating conditions according to the invention led to partial conversion of ethanol to DEE and made it possible to reduce the energy consumption of ethylene production significantly.

DESCRIPTION OF THE INVENTION

The invention relates to a process for dehydration of an ethanol feedstock to ethylene comprising:
- a) a step of preheating said ethanol feedstock to a temperature comprised between 100 and 130° C. by heat exchange with the effluent from step e),
- b) a step of pretreating the ethanol feedstock on an acidic solid operating at a temperature comprised between 100 and 130° C. so as to produce a pretreated ethanol feedstock,
- c) a step of vaporizing a vaporization feedstock comprising said pretreated ethanol feedstock and at least a portion of the flow of treated water recycled according to step h) in an exchanger by means of heat exchange with the effluent from the last reactor of step e), said vaporization feedstock being introduced into said vaporization step at a pressure comprised between 0.1 and 1.4 MPa so as to produce a vaporized feedstock,
- d) a step of compressing said vaporized feedstock in a compressor so as to produce a compressed feedstock,
- e) a step of dehydrating said compressed feedstock in at least one adiabatic reactor containing at least one dehydration catalyst and in which the dehydration reaction takes place, operating at an inlet temperature comprised between 350 and 550° C. and at an inlet pressure comprised between 0.3 and 1.8 MPa,
- f) a step of separating the effluent from the last adiabatic reactor of step e) into an effluent comprising ethylene at a pressure below 1.6 MPa and an effluent comprising water,
- g) a step of purifying at least a portion of the effluent comprising water from step f) and separating at least one flow of treated water and at least one flow of unconverted ethanol,
- h) a step of recycling at least a portion of the flow of treated water from step g) upstream of step c).

Feedstock

According to the invention, the feedstock treated in the dehydration process is an ethanol feedstock.

Said ethanol feedstock is advantageously a concentrated ethanol feedstock. By concentrated ethanol feedstock is meant an ethanol feedstock comprising a percentage by weight of ethanol greater than or equal to 35% by weight. Preferably, said concentrated ethanol feedstock comprises a percentage by weight of ethanol comprised between 35 and 99.9% by weight.

The ethanol feedstock comprising less than 35% by weight of ethanol can be concentrated by any means known to a person skilled in the art, for example by distillation, absorption, or pervaporation.

Said ethanol feedstock also advantageously comprises, in addition to water, a content of alcohols other than ethanol, such as for example methanol, butanol and/or isopentanol, below 10% by weight, and preferably below 5% by weight, a content of oxygenated compounds other than alcohols, such as for example ethers, acids, ketones, aldehydes and/or esters, below 1% by weight and a content of nitrogen and of sulphur, organic and mineral, below 0.5% by weight, the percentages by weight being expressed relative to the total weight of said feedstock.

The ethanol feedstock treated in the process according to the invention is optionally obtained by a process of synthesis of alcohol starting from fossil resources such as for example from coal, natural gas or carbon-containing waste.

Said feedstock can also advantageously originate from non-fossil resources. Preferably, the ethanol feedstock treated in the process according to the invention is an ethanol feedstock produced from a renewable source obtained from biomass, often called "bioethanol". Bioethanol is a feedstock produced by a biological route, preferably by fermentation of sugars obtained for example from crops of sugar-containing plants such as sugar cane (saccharose, glucose, fructose and sucrose), beets, or else from amylaceous plants (starch) or from lignocellulosic biomass or from hydrolysed cellulose (predominantly glucose, and xylose, galactose), containing variable quantities of water.

For a more complete description of the classical fermentation processes, reference may be made to the work "Les Biocarburants, État des lieux, perspectives et enjeux du développement" [Biofuels, appraisal, prospects and development challenges], Daniel Ballerini, Editions Technip.

Said feedstock can also advantageously be obtained from synthesis gas.

Said feedstock can also advantageously be obtained by hydrogenation of the corresponding acids or esters. In this case, acetic acid or acetic esters are advantageously hydrogenated with hydrogen to ethanol. Acetic acid can advantageously be obtained by carbonylation of methanol or by fermentation of carbohydrates.

Preferably, the ethanol feedstock treated in the process according to the invention is an ethanol feedstock produced from a renewable source obtained from biomass.

Preheating Step a)

According to the invention, the ethanol feedstock undergoes a preheating step a) in a heat exchanger so as to produce a preheated ethanol feedstock, by means of heat exchange with the effluent from the dehydration step e) to bring it under the required temperature conditions, between 100 and 130° C., preferably between 110° C. and 130° C., for the pretreatment step b). The pressure of the ethanol feedstock is adjusted, in such a way that the latter is still liquid at the end of the preheating step a), to a value comprised between 0.1 and 3 MPa.

Pretreatment Step b)

According to the invention, the preheated ethanol feedstock undergoes a pretreatment step b) so as to produce a pretreated ethanol feedstock. Said pretreatment step makes it possible to remove the nitrogen-containing compounds present in said preheated feedstock so as to limit the deactivation of the dehydration catalyst located downstream.

Said pretreatment step b) is carried out on an acidic solid, preferably an acid resin, and at a temperature comprised between 100 and 130° C., preferably between 110° C. and 130° C.

Said pretreatment step b) makes it possible to remove the basic and/or organic impurities, and the cationic species, in order to obtain a pretreated ethanol feedstock corresponding to the level of impurities compatible with the dehydration catalyst.

The pretreatment on the acidic solid under the operating conditions according to the invention makes it possible to convert between 3% by weight and 20% by weight, preferably between 8 and 12% by weight of the ethanol present in said feedstock to DEE, the percentage by weight being determined relative to the total weight of ethanol present in said feedstock at the inlet of the pretreatment step b).

The acidic solid includes all the acidic solids known to a person skilled in the art: silica-aluminas, acid clays, zeolites, sulphated zirconias, acid resins, etc. The main thing is that the acidic solid has a high exchange capacity for capturing, as far as possible, the basic and cationic species and an acidity strength high enough to carry out the partial conversion of ethanol to DEE.

Acidic solids that are commonly available commercially are clays treated with acids to make them acidic (such as montmorillonite) and zeolites, having a ratio of silica to alumina in the crystal lattice from 2.5 to 100 molar. The acid resins comprise sulphonic groups, grafted on an organic support composed of aromatic and/or haloaliphatic chains. Preferably the acidic solids have an exchange capacity of at least 0.1 mmol $H^+$ equivalent per gram.

The acid resin includes acidic sulphonic groups and is prepared by polymerization or co-polymerization of aromatic vinyl groups followed by sulphonation, said aromatic vinyl groups being selected from styrene, vinyl toluene, vinyl naphthalene, vinyl ethyl benzene, methyl styrene, vinyl chlorobenzene and vinyl xylene, said resin having a level of cross-linking comprised between 20 and 35%, preferably between 25 and 35% and preferably equal to 30% and an acid strength, determined by potentiometry on neutralization with a KOH solution, from 0.2 to 6 mmol $H^+$ equivalent per gram and preferably between 0.2 and 2.5 mmol $H^+$ equivalent per gram.

Said acidic ion-exchange resin contains between 1 and 2 sulphonic end groups per aromatic group. Its size is comprised between 0.15 and 1.5 mm. By size of the resin is meant the diameter of the smallest sphere circumscribing the particle of resin. The classes of resin size are measured by sieving through suitable sieves according to a technique known to a person skilled in the art.

A preferred resin is a resin consisting of aromatic monovinyl and aromatic polyvinyl copolymers, and very preferably a copolymer of divinyl benzene and polystyrene having a level of cross-linking comprised between 20 and 45%, preferably between 30 and 40%, and preferably equal to 35% and an acid strength, representing the number of active sites of said resin, determined by potentiometry on neutralization with a KOH solution, comprised between 1 and 10 mmol $H^+$ equivalent per gram and preferably comprised between 3.5 and 6 mmol $H^+$ equivalent per gram. For example, the resin is a TA801 resin sold by the company Axens.

The acidic solids can be regenerated from time to time once the exchange capacity is almost saturated by adsorption of basic and cationic species in situ or ex situ. In the case of inorganic acidic solids such as clays and zeolites, regeneration can consist of simple heating at high temperature in order to desorb the basic species in the presence of an inert or oxygen-containing flow. The cations can be removed by ion exchange. The acid resins can be regenerated by ion exchange, typically by liquid-phase treatment with an acid. The acidic solids can also be used once until saturation and replaced with virgin solid.

The acidic solid can be used alone or mixed with other types of acidic solids. Mixtures of different acidic solids or sequences of acidic solids can be used in order to optimize the capacity for adsorbing the basic and cationic species and the capacity for partial conversion of ethanol to DEE.

The pretreatment described above can advantageously be supplemented with a pretreatment using an anion exchange resin. This resin can for example be a resin loaded with sodium, or trimethylammonium, characterized by an exchange capacity measured in mg($OH^-$)/litre. This resin can for example be the resin Amberlite IRN78. This additional resin makes it possible to retain the sulphate ions $SO_4^{2-}$ in order to prolong the catalyst's life.

Vaporization Step c)

The mixture comprising said pretreated ethanol feedstock and at least a portion of the flow of treated water recycled according to the recycling step h) is called the vaporization feedstock.

Preferably, said vaporization feedstock also comprises at least one flow of unconverted ethanol from the step g) of purifying the effluent comprising water.

According to the invention, the dehydration process comprises a step c) of vaporizing said vaporization feedstock so as to produce a vaporized feedstock. Said vaporization is performed by means of heat exchange with the effluent from the dehydration step e) in a heat exchanger.

Preferably, said vaporization feedstock is introduced into said vaporization step c) at a pressure below the pressure of the effluent from the dehydration step e).

The pressure of said vaporization feedstock upstream of the vaporization step c), an essential criterion of the present invention, is advantageously selected to be as high as possible, so that the temperature difference in the heat exchanger between the effluent from the dehydration step e), which is condensing, and said vaporization feedstock, which is evaporating, is at least greater than or equal to 2° C., and preferably at least greater than or equal to 3° C., so as to maximize the heat exchange between said vaporization feedstock and said effluent from the dehydration step e).

This temperature difference in the heat exchanger is called the temperature approach.

Surprisingly, at a given pressure, the vaporization temperature of the vaporization feedstock is lowered compared with that of a feedstock obtained by a sequence of operations that would not include the pretreatment step b). For a given condensation temperature of the effluent from the dehydration step e) and a fixed temperature approach, the pressure upstream of the vaporization step c) can therefore be adjusted to a value higher than it would have been in a sequence of operations not including the pretreatment step b).

The adjustment of said pressure upstream of the vaporization step c) to the highest possible value, within the limits defined in the preceding paragraph, makes it possible to minimize the energy required for compression during the compression step d) of the process according to the invention.

Said vaporization feedstock is introduced into said vaporization step c) at a pressure comprised between 0.1 and 1.4 MPa, preferably between 0.2 and 0.6 MPa.

The introduction of said vaporization feedstock into the vaporization step c) at this level of specific pressure comprised between 0.1 and 1.4 MPa, preferably between 0.2 and 0.6 MPa, below the pressure of the effluent leaving the last reactor of the dehydration step e), makes it possible to take advantage of a vaporization temperature of said vaporization feedstock that is lower than the temperature of condensation of the effluent from the last adiabatic reactor. Thus, most of the latent heat of the aqueous phase of the effluent from the last adiabatic reactor is recovered for vaporizing said vaporization feedstock, without external heat supply. All of the enthalpy of vaporization of said vaporization feedstock is therefore exchanged with the enthalpy of condensation of said effluent.

Compression Step d)

According to the invention, said vaporized feedstock undergoes compression in a compression step d) so as to produce a compressed feedstock. Said compression step d) is advantageously carried out in any type of compressor known to a person skilled in the art. In particular, the compression step d) is advantageously performed in a compressor of the radial compressor type with an integrated multiplier or in a compressor comprising one or more blowers with a radial impeller placed in series without intermediate cooling or in a compressor of the positive-displacement type with or without lubrication.

As step b) makes it possible, surprisingly, to operate at higher pressure upstream of step d), the level of compression necessary in step d) is reduced in order to reach a given pressure at the end of said step d), thus reducing the energy consumption of said step d).

The compression step d) makes it possible to include a heat pump integrated in said process, using the streams from the process, and without using an external heat-transfer fluid.

The combination of the specific operating conditions of step c) and step d) makes it possible to avoid the supply of heat-transfer fluid external to the process to ensure the vaporization of said vaporization feedstock, recovering most of the latent heat of the aqueous phase of the effluent from the last adiabatic reactor for vaporizing the vaporization feedstock. Thus, only the streams from the process are used.

The pressure of said compressed feedstock at the end of the compression step d) is advantageously comprised between 0.3 and 1.8 MPa, preferably between 0.5 and 1.3 MPa. The outlet pressure of said feedstock is high enough for the condensation temperature of the effluent from the last reactor to be above the vaporization temperature of the feedstock entering step c), which is a necessary condition for the feasibility of step c).

Said compressed feedstock from the compression step d) is optionally heated to an outlet temperature comprised between 250 and 420° C. and preferably comprised between 280 and 410° C. in an exchanger of the single-phase gas type, by means of heat exchange with the effluent from the last adiabatic reactor of step e). In said exchanger of the single-phase gas type, said compressed feedstock is superheated and the effluent leaving, in the gaseous state, the last adiabatic reactor of step e) is "desuperheated" without being condensed. After said exchanger of the single-phase gas type, the effluent leaving, in the gaseous state, the last adiabatic reactor of step e) advantageously has a temperature comprised between 180 and 260° C.

Thus, the use of the different exchangers, of the single-phase gas type and gas/liquid evaporator type, and the vaporization, at a pressure below the pressure of the effluent leaving the last reactor, of said vaporization feedstock, makes it possible to condense at least 80% of the steam present in the effluent from the last reactor of the dehydration step e).

Said compressed feedstock, optionally heated in said exchanger of the single-phase gas type, is then advantageously introduced into a furnace so as to bring it to an inlet temperature in at least one adiabatic reactor compatible with the temperature of the dehydration reaction. This exchanger of the single-phase gas type is an exchanger of a type of technology known to a person skilled in the art which makes it possible to minimize the feedstock losses while having a large exchange surface area. This gas/gas exchange at low pressure produces a low heat flux density through the wall of the exchanger (low transfer coefficient), which necessitates having a large exchange surface area. Moreover, the pressure loss must be minimized in order to limit the load on the compressor of step d). For example, this exchanger can be an exchanger with pressurized plates in a shell, of the Packinox type supplied by Alfa Laval.

Dehydration Step e)

According to the invention, said compressed feedstock, optionally heated, undergoes a dehydration step e) in at least one adiabatic reactor which contains at least one fixed bed of dehydration catalyst and in which the dehydration reaction takes place.

The dehydration step e) is advantageously carried out in one or two reactors.

In the case where step e) is carried out in one adiabatic reactor, said compressed feedstock, optionally heated, is advantageously introduced into said reactor at an inlet temperature comprised between 350 and 550° C. and preferably between 400 and 500° C., and at an inlet pressure comprised between 0.3 and 1.8 MPa, and preferably between 0.4 and 0.8 MPa.

The effluent from said adiabatic reactor of step e) advantageously has a temperature comprised between 270 and 450° C. and preferably between 340 and 430° C., and an outlet pressure comprised between 0.2 and 1.6 MPa and preferably between 0.3 and 0.8 MPa.

In the case where step e) is carried out in two adiabatic reactors, said compressed feedstock, optionally heated, is advantageously introduced into the first reactor at an inlet temperature comprised between 350 and 550° C. and preferably at a temperature comprised between 370 and 500° C., and at an inlet pressure comprised between 0.3 and 1.8 MPa, and preferably between 0.4 and 1.1 MPa.

The effluent from the first adiabatic reactor advantageously leaves said first reactor at a temperature comprised between 270 and 450° C. and preferably between 290 and 390° C., and at a pressure comprised between 0.3 and 1.7 MPa and preferably between 0.3 and 1.0 MPa.

Said effluent is then advantageously introduced into a furnace so that the inlet temperature of said effluent in the second adiabatic reactor is comprised between 350 and 550° C. and preferably between 400 and 500° C. Said effluent has an inlet pressure in said second reactor advantageously comprised between 0.3 and 1.7 MPa and preferably between 0.3 and 0.9 MPa.

The effluent from the second adiabatic reactor leaves said second adiabatic reactor at a temperature advantageously comprised between 270 and 450° C. and preferably between 340 and 430° C. The outlet pressure of said effluent from the second adiabatic reactor is advantageously comprised between 0.2 and 1.6 MPa and preferably between 0.3 and 0.8 MPa.

The inlet temperature of the reactor or reactors can advantageously be increased gradually to avoid deactivating the dehydration catalyst.

The dehydration reaction that takes place in at least one adiabatic reactor of step e) of the process according to the invention advantageously operates at a weight hourly space velocity comprised between 0.1 and 20 $h^{-1}$ and preferably between 0.5 and 15 $h^{-1}$. The weight hourly space velocity is defined as the ratio of the mass flow rate of the pure ethanol feedstock to the mass of the catalyst.

The dehydration catalyst used in step e) is a catalyst known to a person skilled in the art. Said catalyst is preferably an amorphous acid catalyst or a zeolitic acid catalyst.

In the case where the dehydration catalyst used in step e) is a zeolitic catalyst, said catalyst comprises at least one zeolite selected from the zeolites having at least pore openings containing 8, 10 or 12 oxygen atoms (8 MR, 10 MR or 12 MR). It is known in fact to define the pore size in zeolites by the number of oxygen atoms forming the annular section of the channels in the zeolites, called "member ring" or MR. Preferably, said zeolitic dehydration catalyst comprises at least one zeolite having a structural type selected from the structural types MFI, FAU, MOR, FER, SAPO, TON, CHA, EUO, MEL and BEA. Preferably, said zeolitic dehydration catalyst comprises a zeolite of the MFI structural type and preferably a zeolite ZSM-5.

The zeolite used in the dehydration catalyst used in step e) of the process according to the invention can advantageously be modified by dealumination or desilication according to any method of dealumination or desilication known to a person skilled in the art.

The zeolite used in the dehydration catalyst used in step e) of the process according to the invention or the final catalyst can advantageously be modified with an agent of a nature such as to attenuate its total acidity and improve its properties of hydrothermal resistance. Preferably, said zeolite or said catalyst advantageously comprises phosphorus, preferably added in the form of $H_3PO_4$ followed by a steam treatment after neutralization of the excess acid with a basic precursor such as for example calcium Ca. Preferably, said zeolite has a phosphorus content comprised between 1 and 4.5% by weight, preferably between 1.5 and 3.1% by weight relative to the total weight of the catalyst.

Preferably, the dehydration catalyst used in step e) of the process according to the invention is the catalyst described in patent applications WO/2009/098262, WO/2009/098267, WO/2009/098268, or WO/2009/098269.

In the case where the dehydration catalyst used in step e) is an amorphous acid catalyst, said catalyst comprises at least one porous refractory oxide selected from alumina, alumina activated with a deposit of mineral acid, and silica-alumina.

Said amorphous or zeolitic dehydration catalyst used in step e) of the process according to the invention can advantageously also comprise at least one matrix of the oxide type, also called binder. By matrix is meant, according to the invention, an amorphous matrix, a crystalline matrix, or a matrix comprising amorphous and crystalline components. Said matrix is advantageously selected from the elements of the group formed by clays (such as for example from the natural clays such as kaolin or bentonite), magnesia, aluminas, silicas, silica-aluminas, aluminates, titanium oxide, boron oxide, zirconia, aluminium phosphates, titanium phosphates, zirconium phosphates, and carbon, used alone or mixed. Preferably, said matrix is selected from the elements of the group formed by aluminas, silicas and clays.

Said dehydration catalyst used in step e) of the process according to the invention is advantageously formed in the form of grains of different shapes and sizes. It is advantageously used in the form of cylindrical or multilobed extrudates, such as bilobed, trilobed, multilobed of straight or twisted shape, but can optionally be manufactured and used in the form of crushed powder, pellets, rings, beads, wheels, or spheres. Preferably, said catalyst is in the form of extrudates.

Said dehydration catalyst used in step e) of the process according to the invention is advantageously used in at least one reactor, in a fixed bed or in a moving bed.

In step e) of the process according to the invention, the catalysts used and the operating conditions are selected so as to maximize the production of ethylene. The overall reactions of dehydration used in step e) of the process according to the invention are as follows:

$$2C_2H_5OH \rightarrow 2CH_2=CH_2 + 2H_2O$$

$$CH_3CH_2OCH_2CH_3 \rightarrow 2CH_2=CH_2 + H_2O$$

The conversion of the ethanol feedstock in step e) is above 90%, preferably 95% and more preferably above 99%.

A conversion below 90% has the effect of lowering the overall yield of the process, as a larger quantity of DEE not converted to ethylene is lost in the downstream separation steps.

The conversion of the ethanol feedstock is defined, as a percentage, by the following formula:

$$[1-(\text{hourly weight of ethanol at outlet/hourly weight of ethanol at inlet})] \times 100.$$

The hourly weight of ethanol at inlet and at outlet is measured conventionally, for example by chromatography.

Step e), in which the dehydration reaction takes place, is advantageously carried out in one or two reactors. A preferred reactor is a radial reactor operating in ascending or descending mode. During step e) of the process according to the invention, conversion of the feedstock is accompanied by deactivation of the dehydration catalyst by coking and/or by adsorption of inhibiting compounds. The dehydration catalyst must therefore undergo a regeneration step periodically. Preferably, the reactor is used in an alternating regeneration mode, also called swing reactor, in order to alternate the phases of reaction and of regeneration of said dehydration catalyst. The objective of this regeneration treatment is to burn the organic deposits as well as the species containing nitrogen and sulphur, contained at the surface and within said dehydration catalyst. The pretreatment step b) used in this invention makes it possible to reduce the quantity of basic and organic impurities, as well as the cationic species that will alter the catalyst's cycle life. The removal of these species thus makes it possible to limit the number of catalyst regenerations.

The regeneration of the dehydration catalyst used in said step e) is advantageously carried out by oxidation of the coke and of the inhibiting compounds under an air flow or under an air/nitrogen mixture, for example using recirculation of the combustion air with or without water in order to dilute the oxygen and control the exothermic nature of regeneration. In this case, the oxygen content at the reactor inlet can advantageously be adjusted with an additional supply of air. The regeneration takes place at a pressure comprised between atmospheric pressure and the reaction pressure.

The regeneration temperature is advantageously selected to be between 400 and 600° C.; it can advantageously vary over the course of regeneration. The end of the regeneration is detected when there is no longer consumption of oxygen, a sign of total combustion of the coke.

The effluent from the last adiabatic reactor of step e) is optionally sent to an exchanger of the single-phase gas type in which it is "desuperheated" without being condensed by heat exchange with the compressed feedstock from step d), which for its part is superheated.

Said "desuperheated" effluent is then advantageously sent to a second exchanger of the gas/liquid type in which it is partially condensed by a heat exchange that serves to vaporize the vaporization feedstock.

Said effluent is then cooled again by heat exchange with the ethanol feedstock during the step a) of preheating the ethanol feedstock.

Separation Step f)

According to the invention, the effluent from the last adiabatic reactor of step e) undergoes a step f) of separation into an effluent comprising ethylene at a pressure below 1.6 MPa, preferably below 0.8 MPa and an effluent comprising water.

The step f) of separating said effluent from the last adiabatic reactor of step e) can advantageously be performed using any method known to a person skilled in the art, such as for example by a zone for gas/liquid separation, and preferably a gas/liquid separating column.

The effluent comprising ethylene at a pressure below 1.6 MPa then advantageously undergoes a compression. Said compression makes it possible to bring the pressure of said effluent back up to a pressure advantageously comprised between 2 and 4 MPa, necessary for its final purification.

At least a portion of the effluent comprising water from step f) is optionally recycled to the separation step f). This recycling makes it possible to increase the effectiveness of step f) by absorbing a portion of the unconverted feedstock. In the case where at least a portion of the effluent comprising water is recycled, said portion of the effluent comprising water is advantageously cooled with a cold fluid or with a fluid from the process and is preferably treated according to the known methods of purification described below.

Purification Step g)

According to the invention, at least a portion of the effluent comprising water from the separation step f) undergoes a purification step g). The purification step g) can advantageously be performed using any method of purification known to a person skilled in the art. As an example, the purification step g) can advantageously be carried out by the use of ion exchange resins, by adding chemicals to adjust the pH, such as for example soda or amines, and by adding chemicals to stabilize the products, such as for example polymerization inhibitors selected from the bisulphites and surfactants.

At least one flow of treated water and at least one flow of unconverted ethanol are then separated. The separation can advantageously be performed using any method of separation known to a person skilled in the art. As an example, the separation can advantageously be carried out by distillation, by the use of molecular sieves, by steam or heat stripping or by solvent absorption, such as for example with glycol-containing solvents.

A flow containing the light gases, preferably acetaldehyde and methanol, can advantageously also be separated.

Recycling Step h)

According to the invention, at least a portion of the flow of treated water from the purification step g) is recycled upstream of the vaporization step c) according to the recycling step h).

The flow of treated water from step g) plays the role of thermal reaction diluent.

The dilution of the pretreated ethanol feedstock by adding at least a portion of the flow of treated water from step g) is performed in a weight ratio of diluent to feedstock advantageously comprised between 1 and 4 with the aim of lowering the ethanol partial pressures in the reactor or reactors and of making the process more selective for ethylene.

At least a portion of said flow of unconverted ethanol from the step g) of purifying the effluent comprising water is advantageously recycled and mixed, upstream of the vaporization step c), with the pretreated ethanol feedstock, and mixed with at least a portion of the flow of treated water recycled according to the recycling step h).

BRIEF DESCRIPTION OF THE FIGURES

FIG. 1 is a diagrammatic representation of the process for dehydration of ethanol in the case of dehydration of a concentrated ethanol feedstock with recycling of at least a portion of the water treated during step h) of the process.

The ethanol feedstock (1) is preheated in an exchanger E1 with the effluent of the last adiabatic reactor R2, which enters via pipeline (14). The preheated ethanol feedstock is then introduced into a pretreatment zone (3) via pipeline (2). The pretreated ethanol feedstock (4) is then mixed in pipeline (5) with a portion of the flow of treated water from the purification zone (20), which is recycled so as to serve as reaction diluent via pipelines (25) and (26). The ethanol feedstock is also mixed with a portion of the flow of unconverted ethanol from the purification zone (20), via pipeline (23), then (26). This mixture, constituting the vaporization feedstock, is introduced via pipeline (5) into a gas/liquid exchanger E2, in which said mixture undergoes heat exchange with the effluent from the last adiabatic reactor R2, which enters the exchanger via pipeline (13) so as to produce a vaporized feedstock. The latent heat, also called enthalpy of condensation, of the effluent from the last adiabatic reactor R2 is used to vaporize the vaporization feedstock, without external heat supply.

The vaporized feedstock is then sent via pipeline (6) to a compressor C1.

Said vaporized and compressed feedstock is then sent via pipeline (7) to an exchanger E3 of the single-phase gas type, in which said feedstock is heated by means of heat exchange with the effluent from the last adiabatic reactor R2, which is introduced into E3 via pipeline (12). In said exchanger of the single-phase gas type, said vaporized and compressed feedstock is superheated and the effluent leaving, in the gaseous state, the last adiabatic reactor R2 is "desuperheated", without being condensed.

Said vaporized and compressed feedstock, heated in the exchanger of the single-phase gas type E3, is then introduced into a furnace H1 via pipeline (8) so as to bring it to an inlet temperature in the first adiabatic reactor R1 compatible with the temperature of the dehydration reaction. The effluent from the first reactor R1 is sent to a second furnace H2 via pipeline (10) before being introduced into the second reactor R2 via pipeline (11).

The effluent from the second reactor R2 then undergoes the three successive exchanges described above in exchangers E3, E2 and E1 via pipelines (12), (13) and (14).

The effluent from exchanger E1 is sent via pipeline (15) to a gas/liquid separating column (16), where it is separated into an effluent comprising ethylene (17) and an effluent comprising water (18). A portion of the effluent comprising water is recycled after cooling to column (16) via pipeline (19).

The portion of the effluent comprising water not recycled to column (16) is sent via pipeline (18) to a step (20) of purification and separation. At least one flow of treated water

(24) and (25) and at least one flow of unconverted ethanol (22) and (23) are then separated. A flow containing the light gases (21) is also separated.

All (optionally a portion) of said flow of unconverted ethanol from the purification step (20) is recycled via pipeline (23) and is mixed with the flow of treated water recycled via pipeline (25) in pipeline (26). The mixture of these two streams is incorporated upstream of exchanger E2 with the pretreated ethanol feedstock (4).

The following examples illustrate the invention without limiting its scope.

EXAMPLES

Example 1

According to the Invention

Example 1 illustrates a process according to the invention.

The ethanol feedstock under consideration is produced by fermentation of wheat, without extraction of glutens, by a process of the dry milling type.

Step a)

Said ethanol feedstock is introduced, at a flow rate of 45,664 kg/h, into an exchanger E1 at a pressure equal to 1.15 MPa and is heated, remaining in the liquid phase, to a temperature of 120° C. against the effluent from the last adiabatic reactor of step e).

Step b)

The heated ethanol feedstock is pretreated on TA801 resin to remove the traces of nitrogen-containing compounds. During this pretreatment, a portion of the ethanol is converted to DEE. The characteristics of the raw ethanol feedstock and of the pretreated feedstock are given in Table 1.

TABLE 1

Characteristics of the ethanol feedstock before and after pretreatment (percentages by weight)

|  | ETHANOL FEEDSTOCK | ETHANOL AFTER PRETREATMENT |
|---|---|---|
| ETHANOL | 91.2% | 82.1% |
| $H_2O$ | 8.7% | 10.5% |
| DEE | 0% | 7.3% |
| NITROGEN-CONTAINING COMPOUNDS | 0.005% | 0.000% |

Step c)

The vaporization feedstock, constituted by the pretreated ethanol feedstock mixed with 141,252 kg/h of treated water and of unconverted ethanol recycled according to step h), is depressurized and introduced into an exchanger E2 at a pressure equal to 0.27 MPa. The bubble point of this feedstock at this pressure is 127° C. taking into account the presence of DEE. The vaporization feedstock enters exchanger E2 at 113° C. and is therefore already vaporized at 8.6% by weight. The pressure at the inlet of exchanger E2 was adjusted in such a way that the temperature approach with the flow from the last adiabatic reactor of step e) is at a minimum of 15° C.

In step c), most of the latent heat of the aqueous phase of the effluent from the last adiabatic reactor of step e) is recovered for vaporizing the vaporization feedstock, without external heat supply. Thus, 93.6 MW is exchanged between said vaporization feedstock and said effluent.

Step d)

The vaporized feedstock is then compressed in a radial compressor with an integrated multiplier so that the pressure of said vaporized feedstock is equal to 0.695 MPa at the end of the compression.

The compressed feedstock is then heated in an exchanger E3 of the single-phase gas type, by means of heat exchange with the effluent from the adiabatic reactor of step e). In said exchanger of the single-phase gas type, said compressed feedstock is superheated to a temperature of 405° C. and the effluent leaving, in the gaseous state, the last adiabatic reactor of step e) is "desuperheated" without being condensed, and has a temperature of 253° C.

Step e)

Said compressed feedstock, heated in said exchanger of the single-phase gas type, is then introduced into a furnace so as to bring it to an inlet temperature in the first adiabatic reactor of step e) compatible with the temperature of the highly endothermic reaction of dehydration and of conversion of DEE to ethylene, i.e. to a temperature of 440° C. The outlet temperature of the last adiabatic reactor of step e) is 420° C.

The trapping of the nitrogen-containing compounds in the pretreatment step b) makes it possible to reduce the inlet temperature of the first adiabatic reactor of step e) significantly.

Said compressed and heated feedstock is introduced into the first adiabatic reactor at an inlet pressure of 0.595 MPa. The pressure of the effluent at the outlet of the last adiabatic reactor of step e) is 0.500 MPa. The dehydration step e) is carried out at a weight hourly space velocity of 7 $h^{-1}$.

The adiabatic reactor contains a fixed bed of dehydration catalyst, said catalyst comprising 80% by weight of zeolite ZSM-5 treated with $H_3PO_4$ so that the content of phosphorus P is 3% by weight.

The conversion of the ethanol feedstock in step e) is 95%.

Step f)

The effluent from the last adiabatic reactor of step e) then undergoes the three heat exchanges described above and is sent to a gas/liquid separating column. An effluent comprising ethylene at a pressure equal to 0.36 MPa is separated, as well as an effluent comprising water. This separation is carried out using a gas/liquid separating column, with recycling of the water produced at bottom of the column to the top of the column and after cooling and injection of neutralizing agent.

The effluent comprising ethylene then undergoes a compression to bring its pressure back up to 2.78 MPa prior to its final purification.

Step g)

A flow of treated water and a flow of unconverted ethanol as well as a flow containing the light gases are then separated by conventional low-pressure distillation of the raw water.

Step h)

A portion of the flow of treated water and a portion of the flow of unconverted ethanol are recycled upstream of the vaporization step c) in the proportions described in step c). The different streams, in kg/h, are presented in Table 2 and in Table 3.

TABLE 2

Composition of the main streams (1/2)

| Description of the flow | Pretreated ethanol feedstock | Flow entering R1 | Flow leaving R2 | Effluent comprising ethylene |
|---|---|---|---|---|
| Corresponding flow No. in the figure | 4 | 9 | 12 | 17 |
| Total mass flow rate kg/h | 45664 | 186916 | 186916 | 25692 |
| Mass flow rate by kg/h components | | | | |
| ethylene | 0 | 0 | 25087 | 25087 |
| ethane | 0 | 0 | 8 | 8 |
| C3 | 0 | 0 | 93 | 93 |
| C4 | 0 | 0 | 87 | 87 |
| DEE | 3352 | 3352 | 14 | 14 |
| ethanol | 37504 | 39310 | 2187 | 151 |
| $H_2O$ | 4808 | 143730 | 158602 | 198 |
| oxygenated compounds (other than ethanol) | 0 | 325 | 586 | 42 |
| Other minor components | 0 | 199 | 252 | 12 |

TABLE 3

Composition of the main streams (2/2)

| Description of the flow | Effluent comprising water | Ethanol and water recycle | Purged water | Light gases |
|---|---|---|---|---|
| Corresponding flow No. in the figure | 18 | 26 | 24 | 21 |
| Total mass flow rate kg/h | 161224 | 141252 | 19007 | 965 |
| Mass flow rate by kg/h components | | | | |
| ethylene | 0 | 0 | 0 | 0 |
| ethane | 0 | 0 | 0 | 0 |
| C3 | 0 | 0 | 0 | 0 |
| C4 | 0 | 0 | 0 | 0 |
| DEE | 0 | 0 | 0 | 0 |
| ethanol | 2036 | 1806 | 3 | 227 |
| $H_2O$ | 158404 | 138922 | 18987 | 495 |
| oxygenated compounds (other than ethanol) | 544 | 325 | 6 | 213 |
| Other minor components | 240 | 199 | 11 | 30 |

Compounds C3 and C4 are C3 and C4 hydrocarbon-containing compounds.

The selectivity of the process for ethylene is 99%.

It is calculated as follows: (Ethylene contained in the effluent comprising ethylene)/(0.61*quantity of ethanol converted) where the quantity of ethanol converted is the ethanol contained in the ethanol feedstock before pretreatment subtracted from the ethanol contained in the streams of purged water and in the effluent comprising ethylene. 0.61 g is the maximum quantity of ethylene obtained on dehydrating 1 g of pure ethanol.

The energy balance of the scheme according to Example 1 according to the invention is presented in Table 4:

TABLE 4

| Energy balance | | | | | |
|---|---|---|---|---|---|
| Energy exchanged within the system | | | Energy supplied to the system by external supply | | |
| Quantity of heat exchanged in the first exchanger (E1) MW | Quantity of heat exchanged in the second exchanger (E2) MW | Quantity of heat exchanged in the third exchanger (E3) MW | Quantity of heat exchanged in the furnace MW | Power required for compression MW | Quantity of heat extracted on the gas/liquid separating column MW |
| 4.21 | 93.6 | 18.32 | 10.4 | 10.9 | 22.53 |

The primary energy consumption was estimated on the following basis:
  efficiency of 0.8 for the furnaces
  efficiency of 0.375 for electricity generation The scheme according to Example 1 according to the invention has an equivalent primary energy consumption or specific consumption of 6.0 GJ equivalent per tonne of ethylene produced.

Example 2

Comparison

Example 2 illustrates a process in which the steps a) and b) of preheating and pretreatment do not take place. The ethanol is not converted to DEE and the process starts at step c); exchanger E1 is no longer present.

Step c)

The vaporization feedstock, constituted by the unpretreated ethanol feedstock mixed with 141,258 kg/h of treated water and of unconverted ethanol recycled according to step h), is introduced at a flow rate of 186,922 kg/h into exchanger E2 at a pressure equal to 0.24 MPa.

The pressure was lowered by 0.03 MPa compared with Example 1. Without the presence of DEE, the bubble point of the vaporization feedstock at 0.27 MPa is 115° C. (127° C. in Example 1). The inlet pressure is altered by 0.03 MPa so as to maintain a minimum temperature approach of 15° C. with the effluent from the last adiabatic reactor of step e).

In step c), most of the latent heat of the aqueous phase of the effluent from the adiabatic reactor of step e) is recovered for vaporizing the vaporization feedstock, without external heat supply. Thus, 98 MW is exchanged between the vaporization feedstock and the effluent from the reactor.

Step d)

The vaporized feedstock is then compressed in a radial compressor with an integrated multiplier so that the pressure of said vaporized feedstock at the end of the compression is equal to 0.695 MPa.

The compressed feedstock is then heated in an exchanger E3 of the single-phase gas type, by means of heat exchange with the effluent from the last adiabatic reactor of step e). In said exchanger of the single-phase gas type, said compressed feedstock is superheated to a temperature of 405° C. and the effluent leaving, in the gaseous state, the last adiabatic reactor of step e) is "desuperheated" without being condensed and has a temperature of 269° C.

Step e)

Said compressed feedstock, heated in said exchanger of the single-phase gas type, is then introduced into a furnace in order to bring it to an inlet temperature in the first adiabatic reactor of step e) compatible with the temperature of the dehydration reaction, i.e. to a temperature of 470° C. The outlet temperature of the last adiabatic reactor of step e) is 420° C.

Said compressed and heated feedstock is introduced into the adiabatic reactor at an inlet pressure of 0.595 MPa. The pressure of the effluent at the outlet of the last adiabatic reactor of step e) is 0.500 MPa. The dehydration step e) is carried out at a weight hourly space velocity of 7 h$^{-1}$.

The conversion of the ethanol feedstock in step e) is 95%.

Step f)

The effluent from the last adiabatic reactor of step e) then undergoes the two heat exchanges described above and is sent to a gas/liquid separating column. An effluent comprising ethylene at a pressure equal to 0.39 MPa is separated, as well as an effluent comprising water. This separation is performed using a gas/liquid separating column, with recycling of the water produced at the bottom of the column to the top of the column and after cooling and injection of neutralizing agent.

The effluent comprising ethylene then undergoes a compression to bring its pressure back up to 2.78 MPa prior to its final purification.

Step g)

The raw water from step f) is then neutralized with soda, then undergoes conventional low-pressure distillation to be separated into three streams: a flow of treated water, a flow of unconverted ethanol and a flow containing the light gases.

Step h)

A portion of the flow of treated water and a portion of the flow of unconverted ethanol are recycled upstream of the vaporization step c).

The different streams, in kg/h, are presented in Table 5 and Table 6.

TABLE 5

Composition of the main streams (1/2)

| Description of the flow | Ethanol feedstock | Flow entering R1 | Flow leaving R2 | Effluent comprising ethylene |
|---|---|---|---|---|
| Corresponding flow No. in the figure | 4 | 9 | 12 | 17 |
| Total mass flow rate kg/h | 45664 | 186922 | 186922 | 25964 |
| Mass flow rate by kg/h components | | | | |
| ethylene | 0 | 0 | 25087 | 25087 |
| ethane | 0 | 0 | 8 | 8 |
| C3 | 0 | 0 | 93 | 93 |
| C4 | 0 | 0 | 87 | 87 |
| DEE | 0 | 0 | 14 | 14 |
| ethanol | 41671 | 43496 | 2187 | 151 |
| H$_2$O | 3993 | 142947 | 158602 | 311 |
| oxygenated compounds (other than ethanol) | 0 | 413 | 586 | 62 |
| Other minor components | 0 | 66 | 258 | 151 |

TABLE 6

Composition of the main streams (1/2)

| Description of the flow | Effluent comprising water | Ethanol and water recycle | Purged water | Light gases |
|---|---|---|---|---|
| Corresponding flow No. in the figure | 18 | 26 | 24 | 21 |
| Total mass flow rate kg/h | 160958 | 141258 | 19007 | 693 |
| Mass flow rate by kg/h | | | | |

TABLE 6-continued

Composition of the main streams (1/2)

| Description of the flow | Effluent comprising water | Ethanol and water recycle | Purged water | Light gases |
|---|---|---|---|---|
| components | | | | |
| ethylene | 0 | 0 | 0 | 0 |
| ethane | 0 | 0 | 0 | 0 |
| C3 | 0 | 0 | 0 | 0 |
| C4 | 0 | 0 | 0 | 0 |
| DEE | 0 | 0 | 0 | 0 |
| ethanol | 2036 | 1825 | 3 | 208 |
| H$_2$O | 158291 | 138954 | 18987 | 350 |
| oxygenated compounds (other than ethanol) | 524 | 413 | 6 | 105 |
| Other minor components | 107 | 66 | 11 | 30 |

Compounds C3 and C4 are C3 and C4 hydrocarbon-containing compounds.

The selectivity of the process for ethylene is 99%.

The energy balance of the scheme according to Example 2 is presented in Table 7.

TABLE 7

Energy balance

| Energy exchanged within the system | | | Energy supplied to the system by an external supply | |
|---|---|---|---|---|
| Quantity of heat exchanged in the first exchanger (E2) MW | Quantity of heat exchanged in the second exchanger (E3) MW | Quantity of heat exchanged in the furnace MW | Electricity required for compression MW | Quantity of heat extracted on the gas/liquid separating column MW |
| 98.0 | 17.1 | 13.9 | 12.4 | 22.53 |

The scheme according to Example 2, as a comparison with the invention, has an equivalent primary energy consumption or specific consumption of 7.23 GJ equivalent per tonne of ethylene produced.

Without pretreatment, the primary energy consumption therefore increases by 1.2 GJ equivalent per tonne of ethylene produced.

The invention claimed is:

1. A process for dehydrating an ethanol feedstock to ethylene comprising:
a) a step of preheating said ethanol feedstock to a temperature between 100 and 130° C. by heat exchange with the effluent from step e),
b) a step of pretreating the ethanol feedstock on an acidic solid operating at a temperature between 100 and 130° C. so as to produce a pretreated ethanol feedstock,
c) a step of vaporizing a vaporization feedstock comprising said pretreated ethanol feedstock and at least a portion of the flow of treated water recycled according to step h) in an exchanger by heat exchange with the effluent from the last reactor of step e), said vaporization feedstock being introduced into said vaporization step at a pressure between 0.1 and 1.4 MPa so as to produce a vaporized feedstock,
d) a step of compressing said vaporized feedstock in a compressor so as to produce a compressed feedstock,
e) a step of dehydrating said compressed feedstock in at least one adiabatic reactor containing at least one dehydration catalyst and in which the dehydration reaction takes place, operating at an inlet temperature between 350 and 550° C. and at an inlet pressure between 0.3 and 1.8 MPa, f) a step of separating the effluent from the last adiabatic reactor of step e) into an effluent comprising ethylene at a pressure below 1.6 MPa and an effluent comprising water, g) a step of purifying at least a portion of the effluent comprising water from step f) and separating at least one flow of treated water and at least one flow of unconverted ethanol, and h) a step of recycling at least a portion of the flow of treated water from step g) upstream of step c).

2. The process according to claim 1, wherein said ethanol feedstock is an ethanol feedstock produced starting from a renewable source obtained from biomass.

3. The process according to claim 1, wherein the vaporization feedstock also comprises at least one flow of unconverted ethanol from step g) of purifying the effluent comprising water.

4. The process according to claim 1, wherein the pressure of the compressed feedstock is between 0.3 and 1.8 MPa.

5. The process according to claim 1, wherein said compressed feedstock is heated in an exchanger of the single-phase gas type, by heat exchange with the effluent from the last adiabatic reactor of step e).

6. The process according to claim 1, wherein the effluent from the last adiabatic reactor of step e) has a temperature between 270 and 450° C. at the outlet of the last adiabatic reactor of step e).

7. The process according to claim 1, wherein the effluent from the last adiabatic reactor of step e) has a pressure between 0.2 and 1.6 MPa at the outlet of the last adiabatic reactor of step e).

8. The process according to claim 1, wherein the dehydration step e) is carried out in one or two reactors.

9. The process according to claim 1, wherein said dehydration catalyst in step e) is an amorphous acid catalyst or a zeolitic acid catalyst.

10. The process according to claim 1, wherein said ethanol feedstock comprises a percentage by weight of ethanol greater than or equal to 35% by weight.

11. The process according to claim 10, wherein said ethanol feedstock comprises a percentage by weight of ethanol between 35 and 99.9% by weight.

12. The process according to claim 1, wherein the pretreatment step b) is supplemented with a pretreatment by an anion exchange resin.

13. The process according to claim 1, wherein the acidic solid is a silica-alumina, acid clay, zeolite, sulphated zirconia or acid resin.

14. The process according to claim 1, wherein the acidic solid has an exchange capacity for capturing basic and cationic species of at least 0.1 mmol $H^+$ equivalent per gram.

15. The process according to claim 1, wherein the acidic solid has acidic sulphonic groups and has been prepared by polymerization or co-polymerization of aromatic vinyl groups followed by sulphonation, said aromatic vinyl groups being selected from the group consisting of styrene, vinyl toluene, vinyl naphthalene, vinyl ethyl benzene, methyl styrene, vinyl chlorobenzene and vinyl xylene, said resin having a level of cross-linking between 20 and 35%.

16. The process according to claim 1, wherein the acidic solid is a copolymer of divinyl benzene and polystyrene having a level of cross-linking between 20 and 45%.

17. The process according to claim 1, wherein the acidic solid is a TA801 resin.

18. The process according to claim 1, wherein step b) is performed at a temperature between 110 and 130° C.

19. The process according to claim 1, wherein step b) is performed at a temperature between 110 and 120° C.

* * * * *